US006723077B2

(12) United States Patent
Pickup et al.

(10) Patent No.: US 6,723,077 B2
(45) Date of Patent: Apr. 20, 2004

(54) CUTANEOUS ADMINISTRATION SYSTEM

(75) Inventors: Ray L. Pickup, Brush Prairie, WA (US); Clement C. Lo, Lake Oswego, OR (US); William D. Noonan, Sherwood, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 09/967,603

(22) Filed: Sep. 28, 2001

(65) Prior Publication Data

US 2003/0065294 A1 Apr. 3, 2003

(51) Int. Cl.$^{7}$ ............................ A61F 13/00; A61K 9/70

(52) U.S. Cl. ........................................ 604/305; 424/449
(58) Field of Search ................................ 604/305–308, 604/310, 19–20; 128/204.24, 200.22, 200.14; 424/446–449; 239/102.2

(56) References Cited

U.S. PATENT DOCUMENTS

| | | | | |
|---|---|---|---|---|
| 3,840,009 A | | 10/1974 | Michaels et al. | |
| 4,250,878 A | | 2/1981 | Jacobsen et al. | |
| 4,596,575 A | | 6/1986 | Rosenberg et al. | |
| 4,683,481 A | | 7/1987 | Johnson | |
| 4,787,888 A | | 11/1988 | Fox | |
| 4,877,745 A | * | 10/1989 | Hayes et al. | 436/166 |
| 4,915,950 A | | 4/1990 | Miranda et al. | |
| 4,938,742 A | | 7/1990 | Smits | |
| 4,944,659 A | | 7/1990 | Labbe et al. | |
| 4,992,808 A | | 2/1991 | Bartky et al. | |
| 5,278,584 A | | 1/1994 | Keefe et al. | |
| 5,391,164 A | | 2/1995 | Giampapa | |

(List continued on next page.)

FOREIGN PATENT DOCUMENTS

| | | |
|---|---|---|
| DK | 19606433 | 8/1997 |
| DK | 19940242 | 1/2001 |
| EP | 0155616 | 9/1985 |
| GB | 2248183 | 1/1992 |
| WO | WO 0106854 | 2/2001 |
| WO | WO 0149360 | 12/2001 |
| WO | WO 9813087 | 12/2001 |
| WO | WO 0243611 | 6/2002 |

OTHER PUBLICATIONS

Acrux Limited, Technical Brief, Jun. 2003.
Hewlett–Packard Company, co–pending U.S. patent application Ser. No. 09/770,723, filed Jan. 25, 2001, entitled: "Two–Step Trench Etch For A Fully Integrated Thermal Inkjet Printhead".
Hewlett–Packard Company, co–pending U.S. patent application Ser. No. 09/823,188, filed Mar. 29, 2001, entitled: "Method and Apparatus for Delivering and Refilling Pharmaceuticals".
Hewlett–Packard Company, co–pending U.S. patent application Ser. No. 10/000,425, filed Oct. 31, 2001, entitled: "Thermal Drop Generator For Ultra–Small Droplets".

*Primary Examiner*—Weilun Lo
*Assistant Examiner*—Linh Trunong

(57) ABSTRACT

Bioactive agents are cutaneously delivered by a jet dispenser using inkjet technology, such as that used in printing. The dispenser propels precise volumes of bioactive agent toward the skin, where they exert a local or topical effect, or move through the skin for transdermal systemic delivery. Drugs are either delivered directly to the skin, or are introduced into a transdermal patch, which may receive repeated dosages. A controller in the dispenser may control delivery of multiple different drugs, timing of drug administration, or change drug regimens in response to a changing medical condition of a patient, such as those monitored by a sensor in communication with the controller, for example to prevent an overdose. The dispenser may act as an electromechanical patch, capable of long term administration of drugs to the skin, to achieve local or systemic pharmaceutical effects. Administration methods are also provided, along with replacement kits.

97 Claims, 5 Drawing Sheets

U.S. PATENT DOCUMENTS

| | | |
|---|---|---|
| 5,474,527 A | 12/1995 | Bettinger |
| 5,511,726 A | 4/1996 | Greenspan et al. |
| 5,582,593 A | 12/1996 | Hultman |
| 5,667,798 A | 9/1997 | Royds et al. |
| 5,739,831 A | 4/1998 | Nakamura et al. |
| 5,782,799 A | 7/1998 | Jacobsen et al. |
| 5,840,062 A | 11/1998 | Gumaste et al. |
| 5,860,957 A * | 1/1999 | Jacobsen et al. ............ 604/156 |
| 5,894,841 A | 4/1999 | Voges |
| 5,925,021 A | 7/1999 | Castellano et al. |
| 5,980,014 A | 11/1999 | Kagami |
| 5,980,934 A * | 11/1999 | Reber et al. ................. 424/449 |
| 6,123,861 A | 9/2000 | Santini, Jr. et al. |
| 6,165,155 A | 12/2000 | Jacobsen et al. |
| 6,206,914 B1 | 3/2001 | Soykan et al. |
| 6,299,900 B1 | 10/2001 | Reed et al. |
| 6,436,078 B1 * | 8/2002 | Svedman .................... 604/313 |
| 6,539,250 B1 * | 3/2003 | Bettinger .................... 604/20 |

\* cited by examiner

CUTANEOUS ADMINISTRATION SYSTEM

INTRODUCTION

This invention relates generally to the administration of compositions (such as pharmaceutical compositions) for cutaneous administration, including transdermal absorption through the skin. In particular, this invention combines the previously unrelated technologies of pharmaceutical administration and inkjet technology.

Pharmaceutical compositions provide effective treatments for a variety of illnesses. Unfortunately, there are many obstacles to the administration of therapeutically effective doses of many medications. For example, some drugs (particularly peptide based drugs such as insulin) are partially or totally inactivated following oral ingestion, by the highly acidic environment of the stomach. Another problem is the "first pass" effect, which refers to the partial inactivation of orally ingested drugs in the liver, after they have been absorbed from the gastrointestinal system, but before they have exerted their full therapeutic effect. Even when these problems are overcome, patients often fail to take their medications at the proper prescribed intervals, or for the necessary period of time, to achieve an optimal therapeutic response.

Inhalational and intranasal administration have been used as alternative routes of drug delivery. Inhaled drugs can be absorbed directly through the mucous membranes and epithelium of the respiratory tract, thereby minimizing initial inactivation of bioactive substances by the liver. Inhalational delivery can also provide drugs directly to therapeutic sites of action (such as the lungs or the sinuses). This mode of administration has been particularly effective for the delivery of pulmonary drugs (such as asthma medications) and peptide based drugs (usually via intranasal administration), using metered dose inhalers (MDIs). However, MDIs often require coordinating inspiration with actuation of the MDI, and some patients are not able to master this technique. Moreover, patients still often forget to take the medication at prescribed times, or for the necessary period of time to achieve clinical goals. Other patients inadvertently or inappropriately use medications, leading to hospitalizations, morbidity, and even death.

In an effort to overcome such problems, some drugs are administered by passive cutaneous routes, such as transdermal delivery of drugs from a patch applied to the skin. Examples of drugs that are routinely administered by this route are nitroglycerin, steroid hormones, and some analgesics (such as fentanyl). Transdermal administration avoids initial inactivation of drugs in the gastrointestinal tract, and provides continuous dosages usually over a relatively short period of time (such as a day), without requiring active participation by the patient. Continuous sustained administration provides better bioavailability of the drug, without peaks and troughs, and eliminates the problem of the patient forgetting to take multiple doses of the drug throughout the day. However the patch must be changed regularly, usually each day, to provide a necessary drug concentration in the patch to establish the correct concentration gradient for delivery of the appropriate dose of the drug across the skin.

In addition to transdermal systemic delivery of drugs, topical delivery of drugs to the surface of the skin is also used for treating many skin conditions. For example, antibiotics are topically administered to the skin to treat infection, anesthetics to treat pain, retinoids to treat acne, and minoxidil to treat hair loss. These drugs must be repeatedly applied to the skin to achieve their effect, and much of the dosage may be lost by drainage of liquid from the application site, or being inadvertently wiped away. Moreover, excess drug is usually applied to the skin, which can lead to undesired toxic effects particularly if the drug is absorbed through the skin.

Devices and methods are disclosed herein for improving the cutaneous delivery of drugs, by using inkjet-like applicators for transdermal and other cutaneous delivery of drugs. Kits and systems for administrating drugs in this fashion are also described.

DETAILED DESCRIPTION OF PARTICULAR EXAMPLES

Figure 1:
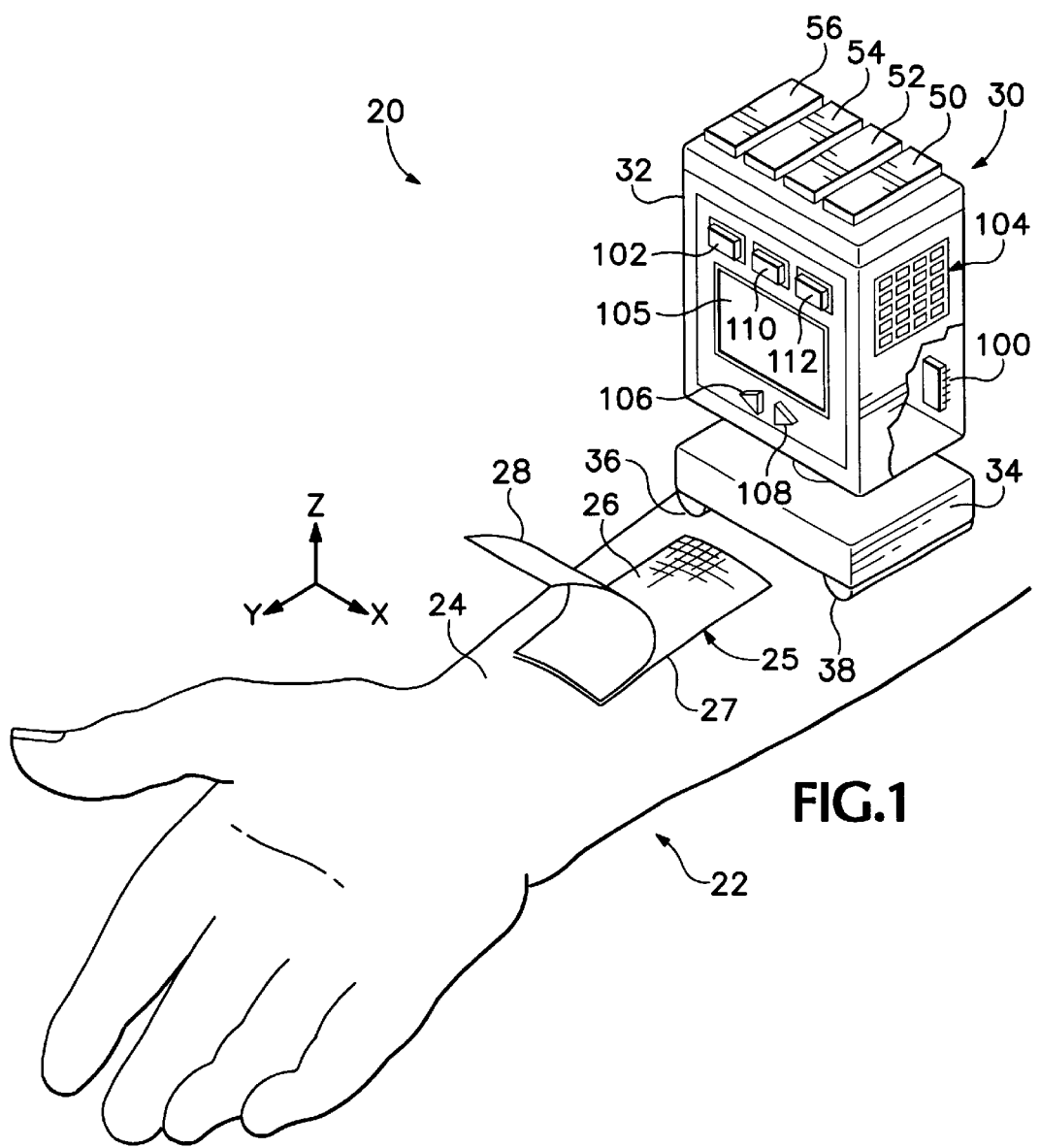
FIG. 1 is a perspective, fragmented, and partially schematic, view of one form of a transdermal application system illustrated herein, having a dispenser and a transdermal patch applied to a human arm.

Unless otherwise noted, technical terms are used according to conventional usage. Definitions of common terms in pharmacology may be found in *Remington: The Science and Practice of Pharmacy*, 19$^{th}$ Edition, published by Mack Publishing Company, 1995 (ISBN 0-912734-04-3). Transdermal delivery is discussed in particular at page 743 and pages 1577–1584.

The singular forms "a," "an," and "the" refer to one or more than one, unless the context clearly dictates otherwise. The term "comprising" means "including."

An "array" refers to a predetermined pattern, which can be either regular or irregular. Examples of arrays are linear distributions or two-dimensional matrices.

A "bioactive" composition, substance or agent is a composition which affects a biological function of a subject to which it is administered. An example of a bioactive composition is a pharmaceutical substance, such as a drug, which is given to a subject to alter a physiological condition of the subject, such as a disease. Bioactive substances, compositions and agents also include other biomolecules, such as proteins and nucleic acids, or liposomes and other carrier vehicles that contain bioactive substances.

"Cutaneous" refers to the skin, and "cutaneous delivery" means application to the skin. This form of delivery can include either delivery to the surface of the skin to provide a local or topical effect, or transdermal delivery, in which a drug diffuses through the skin surface and into the underlying microvasculature, often for systemic administration of the drug.

The present disclosure concerns an applicator for cutaneous delivery of a bioactive composition using a jet dispenser, such as a piezoelectric or thermal jet dispenser, for instance of a construction used in the inkjet printing arts. The dispenser includes a container for holding the bioactive agent and delivering it to a dispenser orifice, or an array of dispenser orifices. The thermal or piezoelectric jet propels precise amounts of droplets from the dispenser toward a cutaneous target. In one embodiment, a spacer is also provided between the dispenser orifice and a cutaneous target, to space the dispenser a desired distance away from the cutaneous target during delivery of the bioactive agent. This spacer may be attached to either the skin or the dispenser, or merely be interposed between them, to provide an interface across which the bioactive substance may be distributed from the orifice, or from an array of orifices, to a cutaneous target. The target may include skin or a skin patch, such as a transdermal drug delivery patch, which acts as a reservoir for subsequent prolonged transdermal delivery of the agent.

In certain embodiments, the dispenser includes the bioactive agent in the container. Examples of agents that can be included in the container include pharmaceutical compositions that are capable of transdermal delivery. Such agents include drugs having sufficient lipophilicity or hydrophilicity to move through the skin surface and stratum corneum. Certain of these agents are designed to reach the microvasculature of the skin, for subsequent systemic absorption and distribution. Examples of agents that are suitable for transdermal delivery include scopolamine, nitrates such as nitroglycerine, an antihypertensive or anti-adrenergic drug such as clonidine, steroid hormones such as 17-beta-estradiol and testosterone, analgesics, such as the opioid analgesic fentanyl, and treatments for nicotine withdrawal, such as nicotine. Many analogues of these drugs retain their biological activity, and are also suitable for transdermal delivery. Although the disclosed dispenser is particularly suited for transdermal delivery of drugs, it can also be used for topical surface application of drugs, such as antibiotics, corticosteroids, minoxidil or retinoids (such as Retin A).

The dispenser may also include a controller for manually or automatically dispensing the bioactive substance from the dispenser at selected times. The controller may take the form of an actuator that is manually depressed to activate the dispenser and dispense the agent. Alternatively, the controller may be a microprocessor which is programmed to dispense the bioactive substance at predetermined intervals, for example several times a day, directly on to the skin or on to a patch. Alternatively, the controller can be used to adjust dosages of drug administered, for example for a particular time of day, an event (such as an activity that will require a dosage modification), or detection of a physiological condition (such a an adverse drug reaction that requires reduction or cessation of drug administration). When the dispenser is used with a patch, the dispenser may be used to recharge the patch and avoid the necessity of changing the patch as often. Either with or without a patch, complex administration protocols may be followed, for example applying different drugs at different times throughout the day or longer period, for example as long as a week, a month, or even longer.

In certain examples, the container may carry multiple container modules, such as removable and replaceable modules that contain the bioactive agent(s). Several modules may contain the same or different agents, for example different agents that combine before or at the time of delivery to modify one or both of the agents, or to produce a desired bioactive effect. An example of a modifying substance that may be combined at the point of ejection is a penetration enhancer that improves cutaneous penetration of the other bioactive substance. Penetration enhancers that may be mixed with a bioactive agent at the time of delivery include solvents such as water; alcohols (such as methanol, ethanol and 2-propanol); alkyl methyl sulfoxides (such as dimethyl sulfoxide, decylmethyl sulfoxide and tetradecylmethyl sulfoxide); pyrrolidones (such as 2-pyrrolidone, N-methyl-2-pyrroloidone and N-(2-hydroxyethyl) pyrrolidone); laurocapram; and miscellaneous solvents such as acetone, dimethyl acetamide, dimethyl formamide, and tetrahyrdofurfuryl alcohol. Other penetration enhancers include amphiphiles such as L-amino acids, anionic surfactants, cationic surfactants, amphoteric surfactants, nonionic surfactants, fatty acids and alcohols. Additional penetration enhancers are disclosed in Remington: The Science and Practice of Pharmacy, 19$^{th}$ Edition (1995) on page 1583. Of course agents such as penetration enhancers can also be premixed with the bioactive agent prior to the point of ejection, for example the bioactive agent and modifying substance can be present together in the container.

The bioactive agent may be any flowable fluid (for example a liquid, gel or powder), although liquids are particularly of use in the dispenser. In some embodiments, at least one of the container modules may contain a bioactive agent in powder or other dry form. The powder or other agent is dispensed from the container, and may be combined with a liquid (such as a penetration enhancer) en route to the cutaneous delivery site. The interface provided by a spacer between the orifice plate and the target allows chemical reactions to occur, as well as phase changes to stabilize (such as a change from a solid to a liquid state). This interface may also provide flexibility in the distribution of the drug across a larger target area, as compared to application of the agent from an orifice that abuts the target. Using existing inkjet technology, distribution of the drug to the target may be carefully controlled, and exact dosing of the drug may be achieved. Controllers may be used to dispense simple or complex drug regimens, which is of particular advantage in patients who require numerous daily medications. Computerized control of medication dosing, which may be programmed by medical personnel for subsequent automated delivery, can help avoid toxic drug interactions, overdosages, and deaths.

The applicator is suitable for use in a variety of ways. For example, the applicator may be intermittently applied to the skin to administer a dosage of a drug directly to the skin. Alternatively, the applicator may be applied to a transdermal patch to recharge it with medication, instead of replacing the patch. In another embodiment, the applicator may be selectively retained in prolonged contact with the cutaneous target, for example by securing the applicator to the skin with an attachment member, such as a strap or adhesive. In this manner, the active agent may be administered from the dispenser for a prolonged period of time into a transdermal patch, or directly onto the skin. A replaceable container module may be removed from the applicator and replaced, to avoid the necessity of removing the applicator from the patient.

In some embodiments, the applicator forms a substantially sealed chamber directly against the skin, without an intervening transdermal patch, and effectively become a direct cutaneous or transdermal applicator. In particularly effective embodiments, an elastomeric seal (such as a continuous seal) is provided between the applicator and the skin to form the sealed chamber in which the drug can be maintained until it is absorbed. Conditions in the sealed chamber may be altered to enhance absorption of the drug, for example by increasing humidity in the chamber by dispensing water droplets, or intermittently applying a penetration enhancer to the skin from the dispenser.

One particularly disclosed embodiment of the device includes a piezoelectric or thermal jet dispenser that includes a plurality of removable modules in fluid communication with one or more fluid orifices (such as an array of orifices) ejecting and directing a pharmaceutical fluid from the modules toward a cutaneous target. A spacer may be carried by the dispenser and positioned to be disposed against the cutaneous target while the dispenser ejects the pharmaceutical fluid from the dispenser. A programmable microprocessor in the dispenser may control ejection of the pharmaceutical fluid from the orifice plate at pre-selected intervals, such as every three or four hours, or even every few minutes or seconds, or ejection can be triggered by a sensor or other feedback mechanism.

The device may further include a programming module, such as a keyboard for entering dosage information, a display screen for showing what information has been entered, and indicators (such as one or more lights or a display screen on the exterior of the device) that provide information about how much drug remains in the device. Display screens may also provide information about medications in the device, and provide an interface through which other information about the medications or their administration can be entered and/or obtained.

The following detailed description of the device is illustrated in the accompanying figures.

Figure 2:
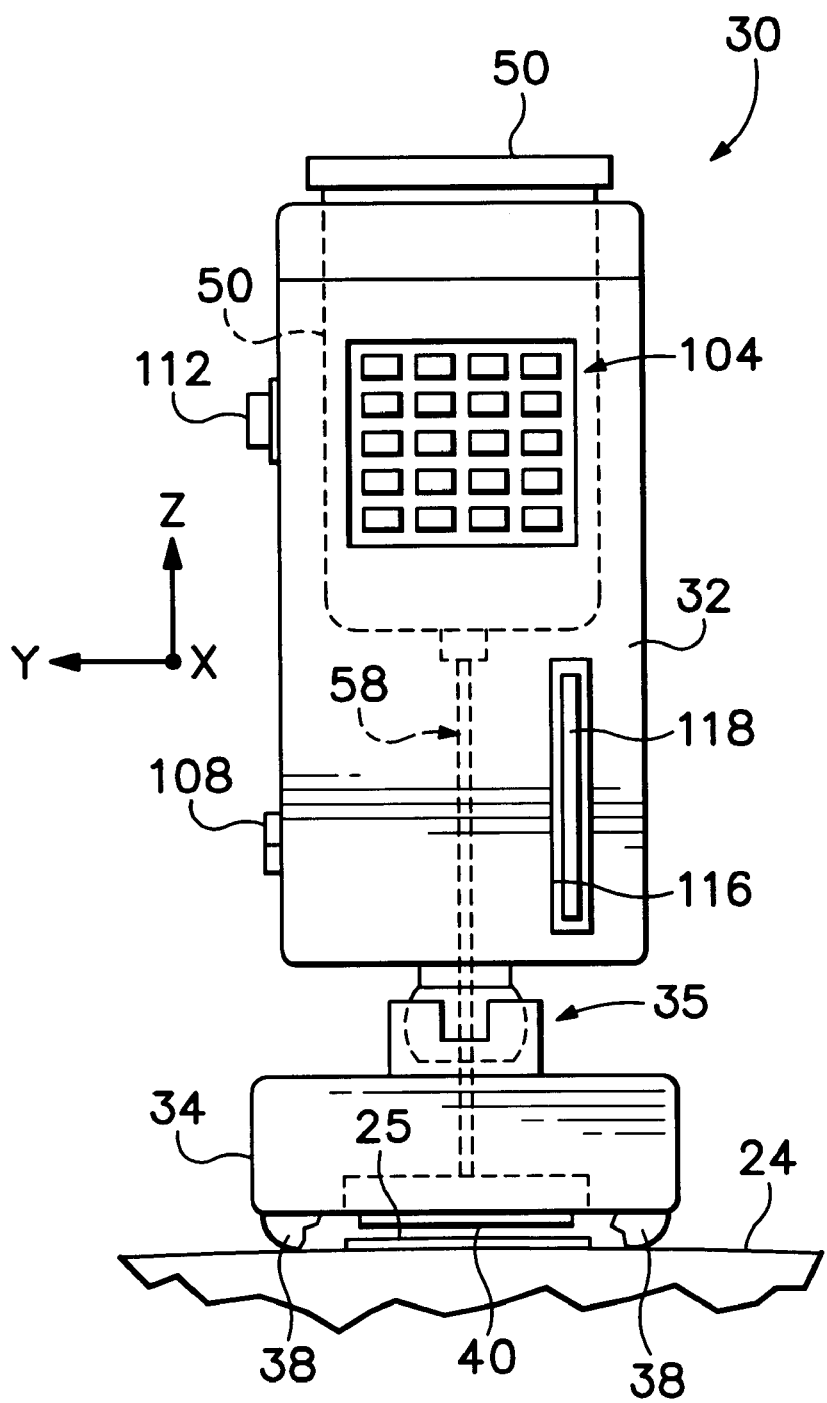
FIG. 2 is an enlarged, side elevational view of the transdermal application system of FIG. 1, shown in place over a transdermal patch for dispensing.
Figures 3, 4:
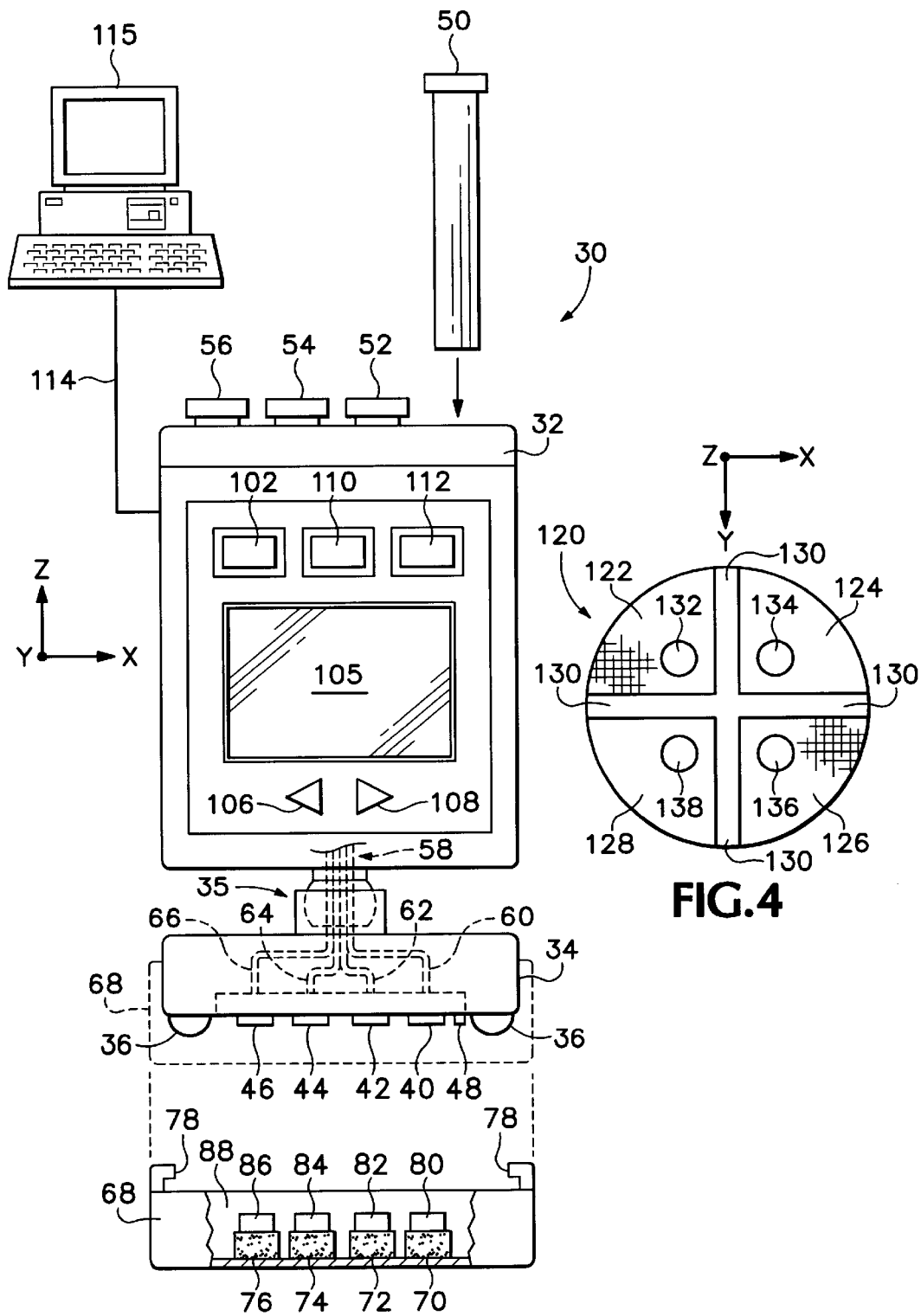
FIG. 3 is an enlarged, front elevational view of the dispenser of FIG. 1, showing a container module removed from the applicator and a protective cap for placement on the droplet head during periods of inactivity. This figure also schematically illustrates how the applicator may be connected to a remote control device, such as a computer.
FIG. 4 is a top plan view of another form of a transdermal patch, which may be used in conjunction with the transdermal application system of FIG. 1.

Embodiment of FIGS. 1–3

The medication dispensers disclosed herein may be similar to liquid dispensers known as inkjet printheads used in inkjet printing mechanisms, such as printers, plotters, facsimile machines and the like, some of which are described for example in Durbeck and Sherr, Output Hardcopy Devices, Academic Press Inc., 1987 (ISBN 0-12-225040-0), particularly in chapter 13, pages 311–370. These technologies have in common the extraction of small quantities of a fluid from a reservoir, which are converted into fine droplets, and transported through the air to a target medium by appropriate application of physical forces. This technology has been implemented in a variety of ways, but one of the common approaches has been thermal inkjet technology, in which liquids are heated using resistors to form drops and propel them from a chamber through an orifice toward a target. Another approach is piezoelectric inkjet technology, in which movement of a piezoelectric transducer changes a chamber volume to generate the drop. An additional approach is known as silicon electrostatic actuator ("SEA")

inkjet technology, such as that disclosed in U.S. Pat. No. 5,739,831 to Nakamura (assigned to Seiko Epson Corporation).

A typical jet printing mechanism uses cartridges (often called "pens") which shoot drops of liquid colorant (generally referred to as "ink") onto a page. Each cartridge has a printhead formed with very small nozzles through which the ink drops are fired. Most often, the printhead is held in a carriage which slides back and forth along a guide rod in a reciprocating printhead system, with a target or print media, such as paper, being advanced in steps between each pass of the printhead. To print an image on media, the printhead is scanned back and forth across the page, shooting drops of ink in a desired pattern as it moves. Other printing systems known as "page-wide array" printers, extend the printhead across the entire page in a stationary location, and print as the media advances under the printhead. The particular liquid ejection mechanism within either type of printhead may take on a variety of different forms known to those skilled in the art, such as the piezoelectric or thermal printhead technology.

For instance two thermal ink ejection mechanisms are shown in U.S. Pat. Nos. 5,278,584 and 4,683,481, both assigned to the present assignee, Hewlett-Packard Company. In a thermal system, a barrier layer containing fluid channels and vaporization chambers is located between a nozzle orifice plate and a substrate layer. The substrate layer typically contains linear arrays of heater elements, such as resistors, which are energized to heat ink within the vaporization chambers. Upon heating, an ink droplet is ejected from a nozzle associated with the energized resistor. By selectively energizing the resistors as the printhead moves across the page, the ink is expelled in a pattern on the print media to form a desired image (e.g., picture, chart or text).

In piezoelectric inkjet technology, an activating pulse is applied to a piezoelectric plate or member attached to a plate, which then responds by flexing to propel an ink drop out of a nozzle. Several examples of piezo-electric inkjet printheads are described in U.S. Pat. Nos. 4,992,808; 6,186,619; and 6,149,968 (assigned to Xaar Technology Ltd.) and U.S. Pat. No. 6,193,343 and WO 00/16981 (assigned to Seiko Epson Corporation).

Some printhead designs use "snapper" reservoir systems, in which permanent or semi-permanent printheads are used in conjunction with a detachable reservoir carrying a fresh liquid supply, with the reservoir being snapped into place on the printhead. Another design uses permanent or semi-permanent printheads in what is known in the industry as an "off-axis" printer. In an off-axis system, the printheads carry only a small liquid supply reciprocally back and forth across the printzone, with this on-board supply being replenished through tubing that delivers liquid from an "off-axis main reservoir" placed at a remote, stationary location within or near the printhead. In both the snapper and off-axis systems, rather than purchasing an entire new cartridge which includes a costly new printhead, the consumer buys only a new supply of liquid for the main reservoir.

In striving to duplicate the quality of photographic film images, the inkjet industry has focused on decreasing the size of ink droplets ejected from the nozzles, as well as accurately placing these droplets on the print media. For instance, some of the more recent inkjet print cartridges are able to deliver droplets of a size on the order of 0.5–6 picoliters, although larger droplets can also be generated, for example droplets of 10, 50, 100 or more picoliters. The resolution within which currently commercially available inkjet printing mechanisms may place ink droplets on a page is on the order of 1200–4800 dots per inch (known in the industry as a "dpi" rating). Thus, while striving to achieve photographic print quality, inkjet printing technology has become very adept at accurately metering and dispensing fluids. The ability to dispense very small and accurate amounts of fluids (including liquids and powders) is taken advantage of in constructing the transdermal cutaneous application systems illustrated herein.

While these inkjet printheads may be used in the cutaneous application systems illustrated here, rather than using a printing analogy, the printhead will instead be referred to in a more general nature as a "dispenser head" or "applicator head."

FIGS. 1–3 illustrate one embodiment of a transdermal application system 20, constructed in accordance with the present invention, for applying a bioactive substance to a subject, such as to a forearm of an animal or person 22, through the skin 24. While the bioactive agent, which is typically dispensed as a fluid, may be applied directly to skin 24, the illustrated embodiment shows applying the agent to an absorbent member, such as a patch 25 of a fabric or other absorbent material which is adhered to skin 24. Patch 25 has an upper exposed surface 26, and an opposing under surface 27 which is in contact with skin 24. A removable protective layer 28, such as a layer of a liquid impermeable thin polyester, may be selectively removed and reapplied to patch 25. In one particular embodiment, the fluid is applied to patch 25, which then allows skin 24 to gradually absorb the fluid from patch 25.

Any of the many types of transdermal patches may be used, or modified for use with the dispenser. For example the Testoderm® transdermal system (Alza Pharmaceuticals) uses a flexible backing of transparent polyester, and a testosterone containing film of ethylene-vinyl acetate copolymer membrane that contacts the skin surface and controls the rate of release of active agent from the system. The surface of the drug containing film is partially covered by thin adhesive stripes of polyisobutylene and colloidal silicon dioxide, to retain the drug film in prolonged contact with the skin. In the present system, adhesive can be provided on both surfaces of the drug containing film, for example on both upper face 26 and under face 27 of patch 25, so that the flexible polyester backing 28 may be selectively removed to provide access to the drug-containing layer without removing the patch. An adhesive release layer with openings in it can be provided between the patch and backing 28, to help protect upper face 26 of patch 25 during repeated removals of backing 28. Alternatively, the patch may be removed, recharged with the drug, and then reapplied, in which event the impermeable backing 28 may be permanently applied to patch 25. In this case, adhesive need only be present on under surface 27 of patch 25. In yet other embodiments, there may be no impermeable backing, such as layer 28, over patch 25, so, for instance the selected drug may be continually administered, or the absorbency of the patch is sufficient to retain the drug in the patch without an impermeable backing. Further examples of transdermal patches that may be used or modified for use in the present system and method include the Nicoderm® and Duragesic® patch.

The transdermal application system 20 illustrated in FIG. 1 includes an applicator or dispenser 30, which is illustrated as an applicator for dispensing a fluidic chemical composition either directly to skin 24, or to patch 25. The applicator 30 includes a main body 32 which may be coupled to a rectangular application head 34 via a linkage, such as a hollow ball and socket linkage 35 which allows applicator head 34 to pivot with respect to main body 32. To assure even and controlled application of a chemical composition to skin 24 or patch 25, the illustrated applicator head 34 is provided with a pair of spacer bars 36 and 38 at opposing edges of applicator head 34. Alternatively, a series of discrete spacer protrusions or bumps, or roller or wheel assemblies (not shown) may be used. As further alternative embodiments, one or more spacers may be formed on the patch 25, or a separate spacer unit (not shown) may be positioned between the dispenser head 34 and the patch upper surface 26 during delivery of the bioactive agent. While the illustrated applicator 30 includes a separate body 32 and applicator head 34, it is apparent that in some embodiments a simpler design may eliminate linkage 35, such that the applicator is a one-piece member.

As shown in FIG. 3, applicator head 34 includes one or more ejection heads, such as fluid ejection heads 40, 42, 44 and 46. Ejection heads 40–46 may be constructed according to principles in the thermal inkjet technology, using piezoelectric ejection techniques, or other manners of fluid ejection known to those skilled in the inkjet arts. Indeed, the ejection of some chemicals may be benefited by a thermal ink ejection technology, in which elevated temperature can activate the agent. In contrast, other agents may chemically degrade and lose some or all bioactivity when heated in a thermal system, and such compositions would preferably be dispensed using a piezoelectric or other non-thermal ejecting head technology. Preferably, the spacer bars 36, 38 maintain a spacing between the ejection heads 40–46 and the upper exposed surface 26 of the patch 25 or skin 24 of greater than about 30 mil ($30 \times 10^{-3}$ inch), for example 1–3 mm, or even 3–5 mm or more. One preferred spacing of 0.2–2.0 mm after the patch has swollen from soaking up the applied fluid permits a smooth even application of fluid over patch 25. Additionally, this ejection head to receiving surface spacing advantageously protects ejection heads 40–46 from unnecessarily coming into contact with the patch 25, which avoids forcing fibers or other debris from the surface of the patch into the printhead nozzles. Adequate spacing between the nozzles and patch also avoids capillary wicking of drug from the nozzles, than can result in inadvertent or unwanted administration of drug to the patch. Such debris or other fibers in the nozzles could potentially damage the ejection head nozzles, leading to fully or partially blocked nozzles that dispense less fluid than intended. Such debris could also lead to misdirected droplets which would miss the target area on patch 25. Applicator head 34 may also include a feedback mechanism, for instance such as a mechanical sensor or an optical sensor 48 which may be used by applicator 30 in a closed-loop system, as described further below.

The fluid dispensed by ejection heads 40, 42, 44 and 46 may be stored in replaceable fluid reservoirs 50, 52, 54 and 56, respectively. As shown in the specific example of FIG. 3, the reservoirs 50–56 may be inserted into receptacles formed within main body 32. Following insertion of the reservoirs 50–56 into the main body 32, a multi-conduit fluid tubing system 58 delivers fluid from the reservoirs 50–56, through the hollow ball and socket linkage 35, into applicator head 34. As shown in FIG. 3, a multi-conduit system 58 may include four discrete fluid conduits, such as tubing running through applicator head 34, or conduits molded, bored or otherwise formed therein, such as conduits 60, 62, 64 and 66. In the illustrated embodiment, the conduits 60, 62, 64 and 66 deliver fluid from the respective reservoirs 50, 52, 54 and 56 to their respective associated ejection heads 40, 42, 44 and 46.

To maintain ejection heads 40–46 relatively moist and free of clogs during periods of applicator inactivity, the application system 20 may include a protective ejection head storage and/or servicing member 68, which in the illustrated embodiment is rectangularly shaped to mate with the open face of rectangular application head 34. Head storage member 68 has four ejection head sealing members, for example elastomeric or foam caps 70, 72, 74 and 76, which are positioned to seal ejection heads 40, 42, 44 and 46 respectively, for instance, using various printhead cap designs known to those skilled in the inkjet arts. To maintain caps 70–76 against their respective ejection heads 40–46, the storage member 68 may include a securement means, such as a pair of clips 78 that mate with applicator head 34 to selectively connect member 68 to applicator head 34.

In a more sophisticated embodiment, storage member 68 may also include one or more ejection head wipers, such as elastomeric wipers 80, 82, 84 and 86. In one embodiment of the storage member 68 having only caps 70–76, the storage member 68 may be positioned over applicator head 34 by movement in a direction parallel with the Z-axis, with securement member 78 being formed with a snap-fit feature to hold member 68 securely in place, with each of the ejection heads 40–46 resting securely against their respective caps 70–76. Such a capping system having foam caps may be constructed as described in U.S. Pat. No. 5,635,965 currently assigned to the Hewlett-Packard Company. A more sophisticated combination storage and servicing member 68 may have securement member 78 formed so that member 68 is applied over the applicator head 34 in a direction parallel to the negative Y axis, and removed in a direction parallel to the positive Y axis. Such a lateral application of the storage and service member 68 over applicator head 34 allows elastomeric wipers 80–86 to wipe liquid or other residue from ejection heads 40–46 as member 68 is applied, as well as upon removal of the service member after uncapping. When the storage/service member 68 has wiping capability, it may be desirable to have a back wall portion 88 of the service member hinged or otherwise retractable to fold downwardly, so upon installation of member 68 the heads 40–46 first contact wiper blades 80–86, and upon removal of member 68, the last items which contact the heads 40–46 are the wipers 80–86.

As illustrated in FIG. 1, the applicator 30 includes an onboard ejection head controller 100, illustrated schematically for convenience. Controller 100 and ejection heads 40–46 receive power either from an onboard battery storage system, which may be located in either main body 32, applicator head 34, or both. Alternatively, power may be supplied from an external source, such as a standard electrical outlet. Of course, rechargeable or replaceable batteries may be preferred in some embodiments for ease of portability and use. Controller 100 operates to apply firing signals to the ejection heads 40–46, which respond by ejecting fluid from reservoirs 50–56, respectively. In a simple embodiment, applicator 30 may include an ON/OFF power switch 102, to which controller 100 responds by beginning and/or ending a fluid ejection sequence. Alternatively, switch 102 may simply serve as an ON switch, with controller 100 determining the precise amount of fluid to be ejected from heads 40–46, and then stopping ejection automatically after the selected metered amount has been dispensed.

In a more sophisticated embodiment, applicator 30 may include an input keypad 104, such as an alpha or alpha numeric keypad. Using keypad 104, a physician, nurse, pharmacist or other health professional, or the subject 22 to which the fluid will be applied, may input variations in the amount of and types of fluids dispensed by applicator head 34. Applicator 30 may also include a display screen, such as liquid crystal display 105, to indicate which selections have been made using keypad 104. Alternatively, keypad 104 may be eliminated, and the controller 100 programmed to display various selections on screen 105. Use of a pair of scrolling buttons 106 and 108 may allow different instructions or selections to be scrolled across, or up and down along, screen 105, including such information such as desired dosages, frequency, and potential side effects.

Display screen 105 may also indicate various selections along an upper portion of the screen, adjacent buttons 102, 110 and/or 112, allowing a user to then select a particular drug or dosage by depressing one or more of these buttons. Alternatively, depressing one of the buttons could indicate the occurrence of a particular event, such as an adverse medication response that would alter (for example decrease) a subsequent dosage administration, or an event (such as physical exertion) than can signal a need to alter a medication dosage. The controller can also be programmed to prevent unauthorized alteration of dosages, for example an increase in a dosage of a controlled substance above that authorized by the prescribing physician. Alternatively, the controller can permit certain ranges of dosages to be administered, for example various doses of an opioid pain reliever in response to fluctuating pain.

As shown in FIG. 3, a more expedient method of initially programming controller 100, or supplying dosage and other information, may be to use a computer input conductor 114, selectively attachable to a receptacle on main body 32, to couple an external computer, microcomputer or other input device 115 to controller 100. It is apparent that other linkage devices may be used to communicate between external computing device 115 and controller 100, such as by using infrared signals, radio waves, modems, and the like. For example, a patient can download information stored in the device about self-regulated dosage administrations or symptoms experienced (as indicated for example by which buttons have been depressed on the device, and/or the pattern and frequency of the buttons that are pushed). This information can be transmitted over a modem to a physician's or other health care provider's office, where it can be displayed (in electronic or other form) to a health care professional, and appropriate action can be taken. For example, if symptoms are noted to be increasing in spite of administration of a therapeutic amount of a particular drug, consideration can be given to providing a new drug or reconsidering the diagnosis for which the drug has been administered.

Alternatively, as shown in FIG. 2, main body 32 may define an input slot 116 which is sized to receive an input device, such as a flash memory card 118, which carries input data for controller 100. Indeed, use of the flash memory card 118 in conjunction with the controller 100 may result in the only other input device of applicator 30 being the ON/OFF switch 102. Alternatively, the switch may only be an ON switch, with the controller 100 ceasing fluid application after a selected dosage has been administered.

Thus, in one embodiment applicator 30 may only have an ON switch 102, and be completely preprogrammed via an external computer 115, such as at a doctor's office or pharmacy, prior to giving the applicator 30 to a patient. In another embodiment, the applicator 30 may be sold with only an ON switch 102, and with the physician or pharmacy supplying one or more of the fluid reservoirs 50–56 in a kit with a flash memory card 118. In such an example, the kit includes one or more reservoirs 50–56, a flash memory card 118, and may also include a supply of patches 25, or the patches may be purchased separately. Alternatively, any combination of the components can be provided in the kit.

While each of the fluid reservoirs 50–56 may carry different bioactive agents, it may also be convenient to have each reservoir carry the same agent, with controller 100 applying fluid from first reservoir 50 until empty, followed by fluid from a second reservoir 52, and so forth. In such a same-fluid embodiment, it would be preferable for applicator 30 to indicate to the person 22, or an attendant, when fluid is being dispensed from the last reservoir, such as reservoir 56. This indication may take the form of displaying a message on screen 105, or simply by having an indicator light or a series of indicator lights mounted on the main body 32. For example, switch 102 may be back lighted to turn a red color when the supply of active agent in the containers 50–56 is low. Alternatively, the indicator may be an audible signal, such as a beeping sound or a buzzer, or a tactile signal, such as a vibratory or vibrating signal similar to those used on pager devices.

As mentioned briefly above, applicator head 34 may also include an optical sensor 48 constructed to have a variety of different uses. For example, optical sensor 48 may be able to determine whether the storage/service member 68 is in place protecting applicator head 34. When so engaged, it may be practical for the controller 100 to periodically purge fluid from the ejection heads 40–46, to keep the caps 70–76 moist and to purge any blockages of dried or partially drying fluid from the ejection head nozzles, or to prevent any inadvertent or undesired administration of the bioactive agent. Additionally, optical sensor 48 may indicate to controller 100 whether ejection heads 40–46 are located over bare skin 24, or over the exposed surface 26 of patch 25. In some embodiments, to distinguish patch 25 from clothing or other fabric, patch 25 has its exposed surface 26 treated with a visual indicator, such as a coating of infrared or ultraviolet ink which is detectable by the sensor 48.

Embodiment of FIG. 4

Furthermore, the optical sensor 48 may be used in conjunction with a segmented pad 120 shown in FIG. 4. The pad 120 is divided into regions, here shown as four regions 122, 124, 126 and 128, separated from one another by a non-absorbing region 130, shown in this symmetrical embodiment as a plus (+) sign. Each of the four absorbent regions 122, 124, 126 and 128 has an identifying indicia 132, 134, 136 and 138, respectively. The patch 120 may be covered with a moisture impervious layer, such as layer 28 described above. The optical sensor 48 may be used to recognize various identifying indicia 132–138, and apply a selected corresponding fluid from one of reservoirs 50–56 to a selected region 122–128 associated with each of indicia 132–138. For instance, optical sensors which can distinguish the colors of black, cyan, magenta and yellow from one another are disclosed in U.S. Pat. No. 6,036,298. Each of the indicia 132–138 may be a different one of these colors, and controller 100 recognizes each of the different indicia, and dispenses a corresponding fluid agent from ejection heads 40, 42, 44 or 46 to a selected area of the patch associated with the appropriate color. Moreover, if a tint, pigment or other colorant is added to the fluids in reservoirs 50–56, optical sensor 48 may be used to distinguish which agent has previously been applied by applicator 30 to patch 120, allowing the controller to apply more of the same fluid over this area, a different fluid over another area, or no fluid over previously applied areas. Alternatively, changes in color of the substrate may be sensed by optical sensor 48 as a drug leaves patch 120, and this color change may be used to indicate to the controller 100 that additional drug must be dispensed to patch 120.

In some embodiments of patch 120, such as shown in FIG. 4, patch 120 may be constructed of a non-woven material which has selected regions which may be made absorbent, and other regions which may be made non-absorbent. In the illustrated example, patch 120 is divided into four absorbent quadrants 122, 124, 126 and 128 by the non-absorbent border region 130. While a circular patch is illustrated, it is apparent that the patch 120 may have other shapes, and each of the regions 122–128 need not be symmetrical, but may be of differing sizes and/or shapes. One manner of making absorbent and non-absorbent regions in the non-woven fabric arts is to form pad 120 as a multi-layer pad, with the layers bonded together by applying heat along the border region 130. Typically non-woven fabrics, such as those of polyethylene and polyurethane, are moisture impervious when manufactured, with moisture pervious or absorbent regions being formed by applying surfactants in regions 122, 124, 126 and 128.

It may be preferable in some embodiments to provide various indicia or markings on pad 120, such as indicia 132, 134, 136 and 138 appearing within the absorbent quadrants 122, 124, 126 and 128, respectively. Indicia 132–138 may be fashioned to change color after administration of the bioactive agent to the pad 120. Thus, a user of a single agent system may apply the agent at different times of the day. Rather than continually tearing off a depleted patch and replacing it with a new one, a situation which may be bothersome, time consuming and irritating or painful, a single patch 120 may be used throughout the day, with fluid applied at various intervals (such as prescribed intervals) to the different quadrants 122–128. The patch 120 may be replenished daily or at even longer intervals, to prolong the effective life of the patch. In some embodiments, a single patch might be retained in place for days or even months.

Moreover, by allowing indicia 132–138 to change color, or otherwise change appearance after application of the bioactive agent, a patient 22 would have a clear visual indicator or reminder as to whether or not a certain dosage had been administered. Alternatively, indicia 132–138 may be color coded, or otherwise provided with indicia displayed on the various fluid reservoirs 50–56. For example, each indicium may be a color that corresponds to a color of a fluid reservoir 50, 52, 54 or 56, or a distinctive shape cut in a release layer on top of pad 120, such as the letters A, B, C and D, each of which may correspond to a particular fluid reservoir. An external surface of each reservoir can also be provided with identifiers, such as bar codes, that are recognized by an optical sensor in the dispenser, to assure that the correct prescribed agent it being dispensed from each reservoir.

Furthermore, while the illustrated applicator 30 has been shown as a rather large box like device capable of dispensing at least four different types of fluids, it is apparent that the configuration of the housing may be simplified and modified to provide a more compact unit, particularly for application of a single fluid. Such a more compact unit may easily be concealed within the palm of ones hand, allowing for more discrete application of the composition, such as when a dosage is required while shopping, in a meeting, or otherwise in public, particularly if the patch is positioned in an accessible location beneath loose fitting clothing.

In use, transdermal patch 25 or 120 is applied to the skin of a subject 22. Impermeable backing 28 is peeled away from patch 25, 120 and applicator 20 is applied to the patch, with spacers 36, 38 resting on the skin. Applicator 20 is then actuated, either manually by pressing switch 102 or automatically by sensors in applicator 20, to apply a bioactive agent from applicator 20 to patch 25, 120. This application can occur several times a day, or at longer intervals. The applicator may be programmed to remind the user (for example by an audible beep) to use the applicator to replenish the supply of drug in the patch 25, 120.

Figure 5:
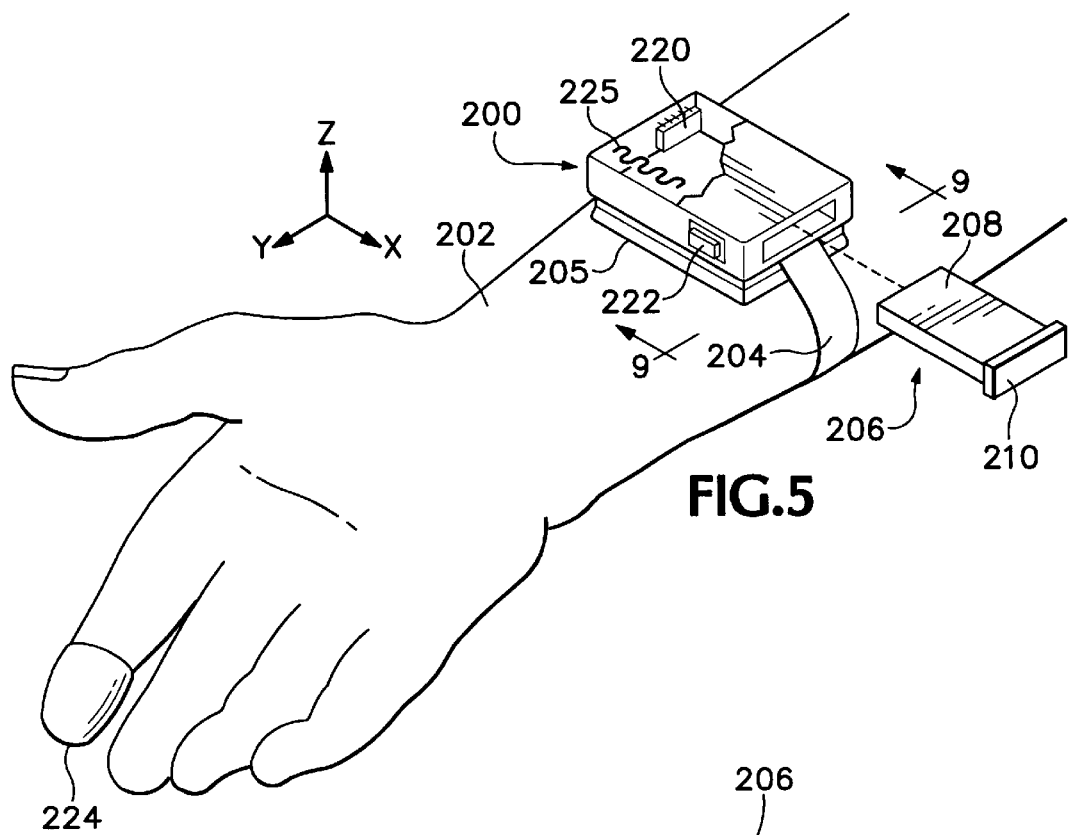
FIG. 5 is a perspective, fragmented, and partially schematic, view of a more compact alternative form of a transdermal application system illustrated herein, having a compact dispenser which may be used with or without a patch, here shown retained against a human arm.
Figure 6:
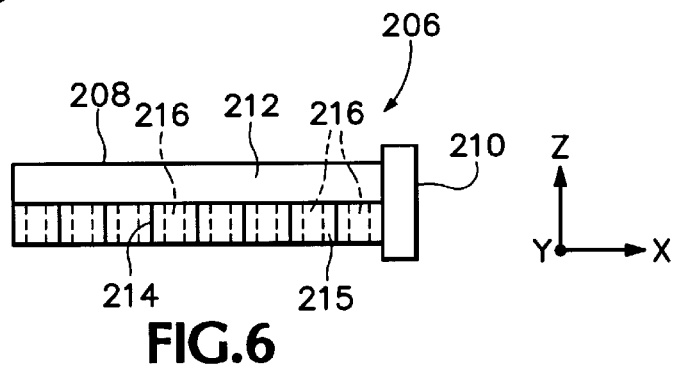
FIG. 6 is a cross-sectional, side elevational view of a removable module of the dispenser of FIG. 5.
Figure 7:
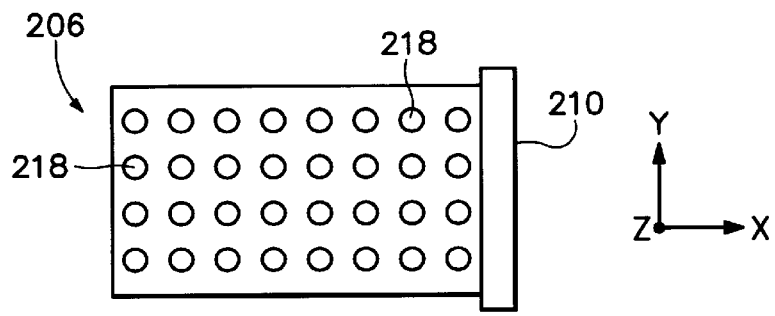
FIG. 7 is a bottom plan view of the module of FIG. 7.

Embodiment of FIGS. 5–7

An example of a more compact dispenser 200 is shown in FIGS. 5–7, in which the dispenser applies a bioactive agent directly to the skin of a subject, without the necessity of an intervening patch. Dispenser 200 is applied to forearm 202 of a subject to whom a bioactive substance is to be administered. In the illustrated example, dispenser 200 is retained in place by a strap 204 which wraps around forearm 202. An elastomeric seal 205 extends around the base of dispenser 200, to simultaneously act as a spacer and form a substantially closed chamber between the ejection head and the skin. Although dispenser 200 is shown attached to an arm 202, it may also be applied to many other parts of the body (such as the torso or leg) which have sufficient permeability to receive the bioactive agent. Many different attachment devices can also be substituted for the strap 204, such as a suction device or adhesive. For example, a relative vacuum can be created within seal 205 to hold dispenser 200 in place, for instance if the seal is formed to act as a suction cup device.

Dispenser 200 includes a removable, replaceable, and/or refillable module 206, which includes a container 208 and an enlarged endplate 210 (or other means to facilitate removal) which may be grasped to manipulate, insert and remove module 206 from dispenser 200. As particularly shown in FIG. 6, container 208 has an upper storage chamber 212 for holding a bioactive liquid (such as a drug), and a lower piezoelectric dispenser portion 214 that includes an array of piezoelectric chambers 215 that communicate with storage chamber 212 through small openings 216. Droplet orifices are also provided through the lower face of dispenser 200, as shown in FIG. 7, to form an array of dispenser orifices 218. At least a portion of one or more walls of each chamber is a piezoelectric member that expands when electrical current is passed through it. The chambers 215 are sufficiently small so that liquid supplied to the chambers 215 from storage chamber 212 remains in each of the chambers 215 (for example by surface tension or back pressure) until the liquid is expelled as a droplet by the expansion of the piezoelectric member. Expansion of the piezoelectric member reduces a volume of the chamber 215 to expel a carefully regulated volume of the liquid.

A controller 220, such as one in the form of a programmable microchip, is attached to an interior wall of dispenser 200. Information may be pre-programmed into controller 220, or controller 220 may be activated by pressing a switch 222 on the exterior of dispenser 200. Alternatively, controller 220 may be programmed by a computer (not illustrated) which communicates with controller 220 through a port (not illustrated) on the exterior of dispenser 200. Controller 220 is capable of selectively activating different piezoelectric members to expel liquid from each chamber, and may also precisely modulate a volume of liquid that is expelled, by regulating a drive signal that passes through the piezoelectric member. Controller 220 may also communicate with one or more remote bio-sensors which monitor one or more parameters of a subject's condition, such as a pulse oximetry device 224 (FIG. 5) shown clipped on a finger of the subject. The pulse oximetry device 224 may provide information about pulse rate and blood oxygenation levels to controller 220 by an electrical lead (not illustrated) or other remote communication device, such as infrared or radiowave communication.

In operation, module 206 is placed in dispenser 200, and dispenser 200 is applied to the skin of the subject and secured in place by latching strap 204 around forearm 202. The elastomeric seal 205 provides a substantially liquid impermeable seal that helps form a closed chamber between dispenser 200 and the skin. Switch 222 is then depressed to activate controller 220, which sends one or more electrical signals to selected piezoelectric members to change shape or other feature a selected number of times, and induce a vibration that discharges one or more droplets of liquid from corresponding piezoelectric chambers 215. The pattern of discharge may be controlled by selectively activating different piezoelectric members, but in one embodiment all the piezoelectric members are simultaneously activated to expel small droplets from all of dispenser orifices 218. Very small liquid droplet sizes may be dispensed in this manner to provide a fine mist of droplets that adhere to the skin, for example by surface tension. The applied liquid then moves through the skin by transdermal flux, to deliver a bioactive agent.

Expulsion of liquid droplets may be repeated at selected intervals, for example every few seconds, minutes, hours or days, to provide a concentration gradient of the drug on the skin surface sufficient to provide transdermal flux across the cutaneous barrier. Generally, the amount of liquid applied is not sufficient to causing a pooling of liquid on the surface of the skin, although such pooling is certainly an option in some embodiments. In this manner, the dispenser can replace a transdermal patch 25, 120, which avoids problems of patch degradation and dislodgment (for example caused by bathing or sweating). Dispenser 200 effectively becomes an electromechanical patch that may in some embodiments be removed for short periods (such as for bathing) and replaced, unlike traditional patches which degrade or become non-adhesive following prolonged use or exposure to moisture. Dispenser 200 may also provide very prolonged administration of a drug, for days, weeks, months, or even years. All that is required is that module 206 be replaced or refilled when depleted.

The electromechanical patch may also be programmed to administer multiple different drugs at different times. In such an embodiment, module 206 may contain multiple liquid sub-compartments that contain different drugs to be administered. The different sub-compartments supply different liquids to different piezoelectric chambers 215, which can be selectively activated to dispense different drugs either simultaneously or at different times. Patients who require complex drug regimens, for example taking multiple different drugs at many different times of day, will benefit from the ability of controller 220 to track and administer the drugs. Moreover, controller 220 may be repeatedly reprogrammed as pharmaceutical dosage regimens are changed in response to a changing medical condition of a subject. Dosage regimens may even be automatically and/or remotely changed in response to varying clinical parameters, such a the results of laboratory tests.

The electromechanical patch 200 provides even greater versatility for substantially immediately responding to the changing medical status of the wearer. Sensors applied to the subject, such as pulse oximetry sensor 224 (FIG. 5), may provide real time feedback to the controller 220 to alter dosage regimens. For example, if one of the drugs to be dispensed is clonidine (which reduces adrenergic stimulation), then sensor 224 provides continuous feedback about pulse rate, which often correlates with a degree of adrenergic stimulation. In a clinically correct situation, the dosage of clonidine administered may be correlated to the pulse rate detected by sensor 224, such that the dosage is increased as pulse rate rises and decreased as pulse rate declines. Alternatively, if the medication being dispensed is an opiate analgesic that has a potential adverse effect on respiratory rate, then further administration of the drug would be halted if blood oxygenation levels fall below a predetermined value, for example 94%.

Although the electromechanical patch dispenser 200 has been described as a substitute for a conventional transdermal patch, it may also be used in conjunction with such a patch 25, 120. In such an embodiment, dispenser 200 is used to apply drug to the patch 25 or 120, which retains the drug against the skin until transdermal flux of the drug occurs. Drug in the patch may be repeatedly replenished by dispenser 200.

In yet other embodiments, the dispenser may be an iontophoretic dispenser, in which ionized drugs are moved through the skin under the influence of an applied electric current. Alternatively, drug movement through the skin can be enhanced by phonophoresis or sonophoresis, in which drug molecules are moved through the skin under the influence of sonic energy, such as ultrasound waves applied to the cutaneous target. Iontophoretic and phonophoretic drug delivery are disclosed in greater detail in *Remington: The Science and Practice of Pharmacy* at page 1584.

While the illustrated embodiment of applicator 200 is shown as being attached to the subject by the strap 204, in other implementations it may be more advantageous to have the applicator 200, perhaps in a smaller or disposable form, attached to the subject by an adhesive tape, for instance under a blouse or a shirt for discrete use. As mentioned above, the applicator 200 may be coupled to a remote sensor, or may include a sensor, such as the optical sensor 48 of FIG. 3, or a mechanical sensor, as mentioned briefly above. For example, a mechanical sensor such as an accelerometer 225 may be used, for instance to monitor physical parameters of a subject, such as a mechanical sensor positioned to monitor heartbeats, breathing for shortness-of-breath/excessively-fast-breathing, or, in a more practical daily application, to monitor a subject's activity. For instance, those jogging or involved in playing sports may need a boost of medication over the dosage used when they are working at a desk, watching television, or sleeping, with the mechanical accelerator sensor 225 monitoring the change in inertia of the individual (bouncing more when active). In response to increased activity signals generated by the mechanical sensor 225, the controller 220 in most instances, administers more medication during these periods of increased activity.

In other embodiments, the applicator 200 may be activated by depressing the button or switch 222, or additional switches, for instance in response to an event to administer an additional dosage or a booster dosage. In such an implementation, the button 222 may be labeled with the event or symptom for which the booster dose is required. For example, the button 222 may be labeled "pain" for addressing pain symptoms, such as chest pains, headaches or nausea, or perhaps "relief" may be a more optimistic label. Examples of events may be eating, strenuous physical activity such as manual labor, playing sports or jogging. Indeed, several buttons may be provided to indicate a variety of events, each of which may administer different dosages or types of medication. As another example, the bioactive composition may not only be one to treat a symptom, but for various physical events, the bioactive composition may be a performance enhancing composition, such as one designed to provide a boost of energy.

Figure 8:
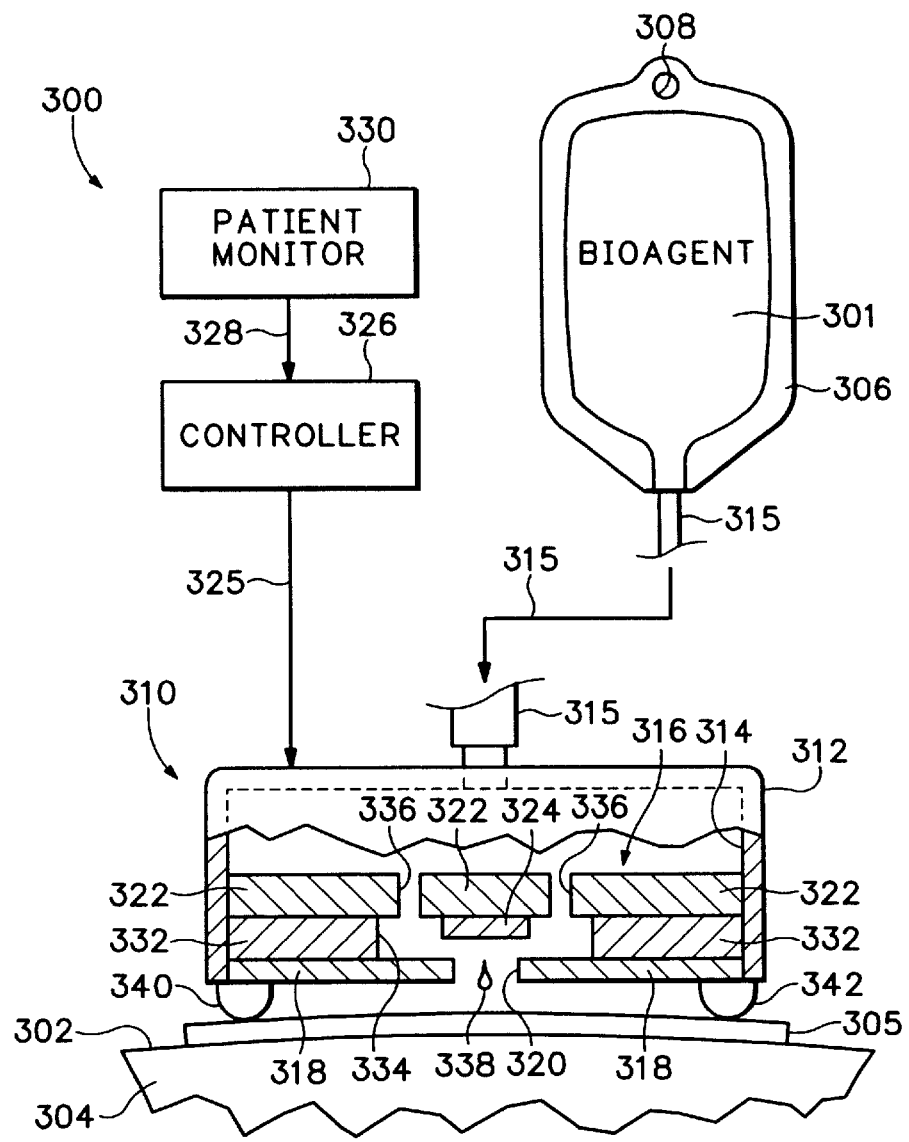
FIG. 8 is a schematic view, partially in cross-section, of an alternative embodiment, in which a bioactive agent is administered from a thermal jet dispenser to a cutaneous target, such as a pad, acting as a substitute for conventional intravenous ("IV") administration of the bioactive agent.
Figure 9:
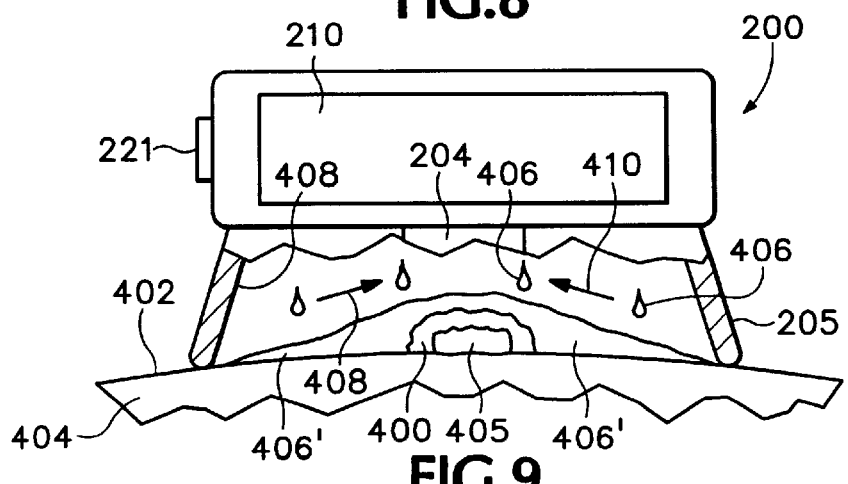
FIG. 9 is a side elevational view, partially in cross-section, of the transdermal application system of FIG. 5, taken along lines 9—9 thereof, showing application of a bioactive-composition-attracting agent, such as a cream, a paste, or a salve to the skin, here on a skin blemish, such as a wart.

Embodiment of FIG. 8

FIG. 8 shows another embodiment of a transdermal application system 300, constructed in accordance with the present invention, for applying a bioactive substance or agent 301 to a skin surface 302 of a subject or patient 304, preferably using a patch 305, which may be constructed as described above for patch 25. The bioactive agent 301 is stored in a remote reservoir, here shown as a flexible bladder 306, such as a plastic bag similar or identical to the containers which are used to administer intravenous ("IV") fluids to patients in hospitals, ambulances, nursing homes, and the like. The illustrated container 306 preferably includes a fixture, such as eyelet 308, which may be used to hang the container from a conventional IV stand, allowing easy substitution of the system 300 for conventional IV's.

The transdermal application system 300 illustrated in FIG. 8 includes an applicator or dispenser 310, which may be constructed as described above for applicators 30 and 200. The applicator 310 in FIG. 8 shows one form of the internal workings of thermal fluid ejecting system, similar to that used in thermal inkjet printheads in the printing arts, for instance of the construction described in U.S. Pat. No. 5,420,627, which is assigned to the present assignee, Hewlett-Packard Company. The applicator 310 includes a main body 312 that defines a feed chamber 314, which receives the bioactive fluid 301 (labeled "bioagent" in FIG. 8) from the ink reservoir 306 by way of a fluid conduit, such as tubing 315, illustrated partially schematically in FIG. 8. A fluid ejection mechanism 316 is preferably located centrally within the chamber 314, and held in place through attachment by an adhesive or other bonding agent to a flexible polymer tape 318, such as Kapton® tape, available from the 3M Corporation, Upilex® tape, or other equivalent materials known to those skilled in the inkjet arts. The illustrated tape 318 serves as a nozzle orifice plate by defining at least one, but preferably more, fluid ejection nozzle hole or orifice 320 formed in tape 318 by, for example, laser ablation technology. The adhesive between the body 312 and the tape 318 may be of an epoxy, a hot-melt, a silicone, a UV curable compound, mixtures thereof, or their structural equivalents.

The ink ejection mechanism 316 includes a silicon substrate 322 that contains for each nozzle 320 an individually energizable thin film firing resistor 324, each located generally behind an associated single nozzle 320. The firing resistors 324 act as ohmic heaters when selectively energized by one or more enabling signals or firing pulses 325, which are delivered from a controller 326 through conductors (omitted for clarity) carried by the polymer tape 318. The controller 326 may operate as described above for controllers 100 and 220 of FIGS. 1 and 5. In the illustrated embodiment of FIG. 8, the controller 326 receives a patient condition input signal 328 from a patient monitoring device 330, which may be a remote bio-sensor monitoring one or more parameters of a subject's condition, similar to the pulse oximetry device 224 of FIG. 5, or a conventional hospital patient monitoring device for gathering information concerning a patient's blood pressure, oxygen level, respiration, etc.

The ink ejection mechanism 316 also includes a barrier layer 332 which may be formed on a surface of the substrate 322 using conventional photolithographic techniques. The barrier layer 332 may be a layer of photoresist or some other polymer, which in cooperation with tape 318 defines a vaporization chamber 334 surrounding an associated firing resistor 324. The barrier layer 332 is bonded to the tape 318 by a thin adhesive layer, such as an uncured layer of polyisoprene photoresist. Fluid 301 from the feed chamber 314 flows through one or more feed channels 336, around the edges of the substrate 322, and into the vaporization chamber 334. When the firing resistor 324 is energized, fluid 301 within the vaporization chamber 334 is ejected, as illustrated by an emitted bioactive fluid droplet 338. In the illustrated embodiment, the fluid droplet 338 is shown traveling through an air gap between the orifice plate tape 318 and the patch 305, with this air gap being defined by spacer members, such as spacers 340 and 342 shown extending from the applicator body 312, for instance in the same manner as described above for spacers 36 and 38 in FIGS. 1–3. Alternatively, an elastomeric lip, such as lip 205 in FIG. 5, may be used instead of spacers 340 and 342, with or without the patch 305.

In operation, the dispenser 310 supplies accurate, metered doses of the bioactive fluid 301 received via tubing 315 at intervals (such as controlled or selected intervals) to the patch 305 when used. The patch 305 absorbs the fluid 301 and retains the fluid against the patient's skin 302 to achieve transcutaneous delivery of the bioactive liquid 301. In this manner, long term administration of the agent 301 to the patch 305 may be achieved, without the necessity of repeatedly applying a dispenser to the patch.

The transdermal application system 300 illustrated in FIG. 8 is particularly suitable for drug administration in a hospital, clinic, or other health care delivery facility in which medication is administered for a prolonged period to a subject. Furthermore, anyone who has had an IV knows it is painful to have a needle inserted into their vein, followed by the pain and annoyance of dealing with the needle remaining taped to their hand while the IV fluid is administered. Emergency medical personal often have to deal with trying to insert an IV needle into a trauma patient with low blood pressure, where locating a viable vein is often difficult. Medical personal treating the elderly or infirm often encounter the same difficulties, with their patients suffering the pain of the needle probing for a vein. Clearly, the transdermal application system 300 alleviates these problems for both patients and medical personal alike by providing a non-invasive method of administering medications or other bioactive agents.

Embodiment of FIG. 9

FIG. 9 shows an alternate embodiment a transdermal application system using the applicator 200 of FIG. 5, for instance, in conjunction with a bioactive composition attracting agent, such as a cream, a paste, or a salve 400 applied to the skin 402 of a subject 404, here on a skin blemish, such as a wart 405. The applicator 200 is shown by way of illustration, and it is apparent that applicators 30 and 310 may also be used with cream 400, shown here without use of a patch 25, 120, 305. Here we see the applicator 200 ejecting bioactive fluid droplets 406 into a chamber 408 defined between the ejection head defining nozzles 218 (see FIGS. 6 and 7), the patient's skin 402, and the sealing lip 205. The droplets 406 accumulate in a puddle 406' which is drawn toward the wart 405 as indicated by arrows 408, 410 by the fluid's affinity with the cream 400. The fluid 406' and the cream 400 mix together so the fluid travels through the cream to contact and treat the wart 405. In this manner, the bioactive-agent-attracting cream 400 assists in drawing or pulling the treatment fluid 408 toward the location to be treated, here, wart 405. Examples of bioactive-agent-attracting creams, pastes or salves include a product sold under the trade name Recepta-gel®, as well as dimethyl sulfoxide ("DMSO"). Such a bioactive composition attracting agent 400 may also enhance the penetration of the bioactive composition 406', for instance, in the same manner as DMSO or glycerin works to enhance transcutaneous flux of the bioactive agent 406' that is delivered to wart 405. Thus, when provided as a refill kit, the a fresh module carrying the treatment fluid 406 may be supplied with a container of the cream 400, for instance in a tear-away container(s), similar to those in which single servings of mustard and ketchup are supplied, or in a resealable tube.

Conclusion

Many other variations of devices and methods are within the scope of this disclosure. For example, instead of mixing a bioactive agent with another agent (such as another bioactive agent, for example a penetrant such as DMSO) at the time of ejection from a jet dispenser, the agents can be mixed prior to ejection (for example, as illustrated in U.S. Pat. No. 5,980,014 assigned to Sony Corporation). Also, instead of mixing bioactive agents prior to delivery, one of the bioactive agents can be applied to the cutaneous surface, or the penetrant can be present in the pad itself. For example, DMSO or other agents can be applied to the skin, or can be present in the patch, to enhance transcutaneous flux of a bioactive agent that is delivered to the skin or pad. Another variation uses the optical sensor 48 to read patient identification, such as a bar code on a patient's hospital identification bracelet, with this patient information then being used by controller 100 to adjust the dosage and/or type of medication administered. Such a system avoids accidentally administering the wrong medication to a patient. As another example, the embodiments shown in the drawings are given to illustrate the principles and concepts covered by the claims below, and it is apparent that the applicator may be constructed larger or smaller than those shown here.

This specification has described several detailed examples, which are not intended to be limiting. Rather, these examples are provided to illustrate some of the embodiments which come within the scope of the following claims.

We claim:

1. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target;

a main body which supports said container; and a dispensing head which supports said orifice;

wherein said dispensing head supports plural orifices each fluidically coupled to said container.

2. An applicator according to claim 1, wherein the spacer is supported by the dispenser.

3. An applicator according to claim 1, wherein the spacer is for attachment to the cutaneous target.

4. An applicator according to claim 1, further comprising an adhesive applicator patch for application to the cutaneous target.

5. An applicator according to claim 1, wherein the applicator is an applicator for transdermal delivery of a bioactive composition capable of transdermal flux.

6. An applicator according to claim 1, further comprising a bioactive composition in the container.

7. An applicator according to claim 6, wherein the bioactive composition is a pharmaceutical composition.

8. An applicator according to claim 7, wherein the pharmaceutical composition is capable of transdermal delivery.

9. An applicator according to claim 1, wherein the dispenser is a thermal droplet jet dispenser.

10. An applicator according to claim 1, wherein the dispenser is a piezoelectric droplet jet dispenser.

11. An applicator according to claim 1, further comprising a controller which automatically ejects the bioactive composition from the dispenser orifice at selected times.

12. An applicator according to claim 11, wherein the controller is a microprocessor programmed to dispense the bioactive composition at predetermined intervals.

13. An applicator according to claim 1, wherein the container comprises multiple container modules.

14. An applicator according to claim 13, wherein the multiple container modules are removable from the dispenser.

15. An applicator according to claim 13, wherein at least two of the container modules contain a bioactive substance.

16. An applicator according to claim 15, wherein at least one of the container modules contains a bioactive agent in powder form.

17. An applicator according to claim 15, wherein at least two of the container modules contain different bioactive substances that combine after ejection to produce a bioactive effect.

18. An applicator according to claim 17, wherein at least one of the bioactive substances is a penetration enhancer that improves cutaneous penetration of another bioactive substance.

19. An applicator according to claim 18, wherein the penetration enhancer is dimethyl sulfoxide (DMSO).

20. An applicator according to claim 15, wherein the bioactive composition is a nitrate, an anti-hypertensive drug, an analgesic, a hormone or an analogue thereof, or nicotine or an analogue thereof.

21. An applicator according to claim 20, wherein:
the dispenser is a piezoelectric droplet jet dispenser; and
the nitrate is nitroglycerin.

22. An applicator according to claim 20, wherein the anti-hypertensive drug is clonidine or minoxidil, the analgesic is fentanyl, or the hormone is estrogen or testosterone.

23. An applicator according to claim 1, further comprising an attachment member for selectively retaining the dispenser in prolonged contact with the cutaneous target.

24. An applicator according to claim 23, wherein the attachment member comprises a strap.

25. An applicator according to claim 23, wherein the attachment member comprises an adhesive.

26. An applicator according to claim 1, wherein:
the spacer comprises a sealing member that for selectively substantially sealing the dispenser against the skin of a subject to form a substantially closed chamber when the dispenser is in contact with the skin.

27. An applicator according to claim 26, wherein the sealing member is a continuous elastomeric seal.

28. An applicator according to claim 1, further comprising an indicator which indicates a degree of depletion of the bioactive composition in the dispenser.

29. An applicator according to claim 1 further comprising:
a bio-sensor which monitors a measurable parameter of a subject and generates a signal in response thereto; and
a controller which automatically dispenses the bioactive composition from the dispenser orifice in response to said signal.

30. An applicator according to claim 29 wherein the bio-sensor comprises a pulse oximetry device.

31. An applicator according to claim 30 wherein said parameter comprises pulse rate.

32. An applicator according to claim 30 wherein said parameter comprises blood oxygenation levels.

33. An applicator according to claim 30 wherein said bio-sensor communicates said signal to the controller by infrared communication.

34. An applicator according to claim 30 wherein said bio-sensor communicates said signal to the controller by radiowave communication.

35. An applicator according to claim 1, further comprising a display which displays information about said composition.

36. An applicator according to claim 1, further comprising an interface which receives a memory storage device containing dosage information concerning administration of said composition.

37. An applicator according to claim 1, further comprising a keypad input which receives dosage information concerning administration of said composition.

38. An applicator according to claim 1, further comprising:
a display which displays information about said composition, including various dosages; and
a keypad input including scroll keys which when activated cause the display to selectively show said various dosages.

39. An applicator according to claim 1, further comprising a controller which is programmable.

40. An applicator according to claim 39 wherein said controller is programmable from a remote computer in communication with said controller.

41. An applicator according to claim 1, further comprising a flexible link which couples together said main body and said dispensing head.

42. An applicator according to claim 41, wherein said flexible link is hollow and contains a fluid conduit which fluidically couples said container to said orifice.

43. An applicator according to claim 1, further comprising a main body which supports said container and said orifice.

44. An applicator according to claim 43, wherein said container is removable from the main body.

45. An applicator according to claim 1, further comprising a sensor.

46. An applicator according to claim 45, further comprising a controller in communication with said sensor.

47. An applicator according to claim 46, wherein:
said sensor comprises an optical sensor;
said target changes color following delivery of the bioactive composition; and
said optical sensor detects said color change and in response thereto, the controller ceases ejection of said composition.

48. An applicator according to claim 46, wherein:
said sensor comprises an optical sensor;
said target changes color following absorption of the bioactive composition; and
said optical sensor detects said color change and in response thereto, the controller causes said orifice to eject said composition.

49. An applicator according to claim 46, wherein:
said sensor comprises an optical sensor;
the container comprises two container modules each containing different bioactive substances;

the target has indicia detectable by said optical sensor indicative of one of said different bioactive substances; and the controller causes said orifice to eject said one of said different bioactive substances.

50. An applicator according to claim 1, further comprising a dermal patch between said orifice and said target.

51. An applicator according to claim wherein the dermal patch is of an absorbent material which receives said delivery of said composition.

52. An applicator according to claim 1, wherein the dispenser comprises a silicon electrostatic actuated droplet jet dispenser.

53. An applicator according to claim 28, wherein said indicator comprises an indicator light.

54. An applicator according to claim 28, wherein said indicator comprises an audible signal.

55. An applicator according to claim 28, wherein said indicator comprises a tactile signal.

56. An applicator according to claim 55, wherein said tactile signal comprises a vibratory signal.

57. An applicator according to claim 45, wherein said sensor comprises an optical sensor.

58. An applicator according to claim 45, wherein said sensor comprises a mechanical sensor which monitors a physical parameter of a subject.

59. An applicator according to claim 58, wherein said mechanical sensor comprises an accelerometer.

60. An applicator according to claim 59, wherein said accelerometer monitors activity of a subject bearing said cutaneous target and adjusts said delivery in response to said monitoring.

61. An applicator according to claim 1, further including an activation device which may be manually triggered to eject said bioactive composition from the jet dispenser.

62. An applicator according to claim 61, further including plural activation devices each bearing a label corresponding to an event, with different dosages of the bioactive composition being ejected from the jet dispenser according to which of the plural activation devices is triggered.

63. An applicator according to claim 61, wherein the jet dispenser contains plural bioactive compositions, and the applicator further includes plural activation devices with different bioactive compositions being ejected from the jet dispenser according to which of the plural activation devices is triggered.

64. An applicator according to claim 1, further including a reservoir containing said bioactive composition and a fluid conduit to convey the bioactive composition from the reservoir to the jet dispenser.

65. An applicator according to claim 64, wherein said fluid conduit comprises tubing.

66. An applicator according to claim 64, wherein said reservoir comprises a collapsible bladder.

67. An applicator for cutaneous delivery of a bioactive composition to a cutaneous target, comprising:
a jet dispenser comprising an orifice, and a container which holds and delivers the bioactive composition to said orifice for ejection therethrough; and
a spacer positioned between the dispenser orifice and the target during ejection of the bioactive composition to the target;
wherein the container comprises multiple container modules and at least two of the container modules contain a bioactive substance, the at least two of the container modules containing different bioactive substances that combine after ejection to produce a bioactive effect.

68. An applicator according to claim 67, wherein at least one of the bioactive substances is a penetration enhancer that improves cutaneous penetration of another bioactive substance.

69. An applicator according to claim 68, therein the penetration enhancer is dimethyl sulfoxide (DMSO).

70. An applicator for cutaneous delivery of a bioactive composition to a cutaneous target, comprising:
a jet dispenser comprising an orifice, and a container which holds and delivers the bioactive composition to said orifice for ejection therethrough; and
a spacer positioned between the dispenser orifice and the target during ejection of the bioactive composition to the target;
wherein the container comprises multiple container modules and at least two of the container modules contain a bioactive substance;
wherein the bioactive composition is a nitrate, an anti-hypertensive drug, an analgesic, a hormone or an analogue thereof, or nicotine or an analogue thereof;
wherein the dispenser is a piezoelectric droplet jet dispenser and the nitrate is nitroglycerin.

71. An applicator for cutaneous delivery of a bioactive composition to a cutaneous target, comprising:
a jet dispenser comprising an orifice, and a container which holds and delivers the bioactive composition to said orifice for ejection therethrough; and
a spacer positioned between the dispenser orifice and the target during ejection of the bioactive composition to the target;
wherein the container comprises multiple container modules and at least two of the container modules contain a bioactive substance;
wherein the bioactive composition is a nitrate, an anti-hypertensive drug, an analgesic, a hormone or an analogue thereof, or nicotine or an analogue thereof;
wherein the anti-hypertensive drug is clonidine or minoxidil, the analgesic is fentanyl, or the hormone is estrogen or testosterone.

72. An applicator for cutaneous delivery of a bioactive composition to a cutaneous target, comprising:
a jet dispenser comprising an orifice, and a container which holds and delivers the bioactive composition to said orifice for ejection therethrough;
a spacer positioned between the dispenser orifice and the target during ejection of the bioactive composition to the target; and
an attachment member for selectively retaining the dispenser in prolonged contact with the cutaneous target;
wherein the attachment member comprises an adhesive.

73. An applicator for cutaneous delivery of a bioactive composition to a cutaneous target, comprising:
a jet dispenser comprising an orifice, and a container which holds and delivers the bioactive composition to said orifice for ejection therethrough; and
a spacer positioned between the dispenser orifice and the target during ejection of the bioactive composition to the target;
wherein the spacer comprises a sealing member that selectively substantially seals the dispenser against skin of a subject to form a substantially closed chamber when the dispenser is in contact with the skin;
wherein the sealing member is a continuous elastomeric seal.

74. An applicator for cutaneous delivery of a bioactive composition to a cutaneous target comprising skin covering a subject having a measurable parameter, the applicator comprising:
- a jet dispenser comprising an orifice, and a container which holds and delivers the bioactive composition to said orifice for ejection therethrough;
- a spacer positioned between the dispenser orifice and the target during ejection of the bioactive composition to the target;
- a bio-sensor which monitors said parameter of the subject and generates a signal in response thereto; and
- a controller which automatically dispenses the bioactive composition from the dispenser orifice in response to said signal;
- wherein the bio-sensor comprises a pulse oximetry device.

75. An applicator according to claim 74 wherein said parameter comprises pulse rate.

76. An applicator according to claim 74 wherein said parameter comprises blood oxygenation levels.

77. An applicator according to claim 74 wherein said bio-sensor communicates said signal to the controller by infrared communication.

78. An applicator according to claim 74 wherein said bio-sensor communicates said signal to the controller by radiowave communication.

79. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target; and
- a controller which is programmable, wherein said controller is programmable from a remote computer in communication with said controller.

80. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target;
- a main body which supports said container;
- a dispensing head which supports said orifice; and
- a flexible link which couples together said main body and said dispensing head.

81. An applicator according to claim 80, wherein said flexible link is hollow and contains a fluid conduit which fluidically couples said container to said orifice.

82. An applicator for cutaneous delivery of a bio active composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target;
- a sensor; and
- a controller in communication with said sensor;
- wherein said sensor comprises an optical sensor, said target changes color following delivery of the bioactive composition, and said optical sensor detects said color change and in response thereto, the controller ceases ejection of said composition.

83. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target;
- a sensor; and
- a controller in communication with said sensor;
- wherein said sensor comprises an optical sensor, said target changes color following absorption of the bioactive composition, and said optical sensor detects said color change and in response thereto, the controller causes said orifice to eject said composition.

84. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target;
- a sensor; and
- a controller in communication with said sensor;
- wherein said sensor comprises an optical sensor, the container comprises two container modules each containing different bioactive substances, the target has indicia detectable by said optical sensor indicative of one of said different bioactive substances, and the controller causes said orifice to eject said one of said different bioactive substances.

85. An applicator for cutaneous delivery of a bio active composition to a cutaneous target, comprising:
- a jet dispenser comprising an orifice, and a container which holds and delivers the bioactive composition to said orifice for ejection therethrough; and
- a spacer positioned between the dispenser orifice and the target during ejection of the bioactive composition to the target;
- wherein the dispenser comprises a silicon electrostatic actuated droplet jet dispenser.

86. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target; and
- an indicator which indicates a degree of completion of the bioactive composition in the dispenser;
- wherein said indicator comprises an indicator light.

87. An applicator for cutaneous delivery of a bioactive composition to a cutaneous target, comprising:
- a jet dispenser comprising an orifice, and a container which holds and delivers the bioactive composition to said orifice for ejection therethrough;
- a spacer positioned between the dispenser orifice and the target during ejection of the bioactive composition to the target; and an indicator which indicates a degree of completion of the bioactive composition in the dispenser;

wherein said indicator comprises an audible signal.

88. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and an indicator which indicates a degree of completion of the bioactive composition in the dispenser;

wherein said indicator comprises a tactile signal.

89. An applicator according to claim 88, wherein said tactile signal comprises a vibratory signal.

90. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and an optical sensor.

91. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and a mechanical sensor which monitors a physical parameter of a subject.

92. An applicator according to claim 91, said mechanical sensor comprises an accelerometer.

93. An applicator according to claim 92, wherein said accelerometer monitors activity of a subject bearing said cutaneous target and adjusts said delivery in response to said monitoring.

94. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and a plurality of activation devices which may be manually triggered to eject said bioactive composition from the jet dispenser, each activation device bearing a label corresponding to an event, with different dosages of the bioactive composition being ejected from the jet dispenser according to which of the plural activation devices is triggered.

95. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and an activation device which may be manually triggered to eject said bioactive composition from the jet dispenser;

wherein the jet dispenser contains plural bioactive compositions, and the applicator further includes plural activation devices with different bioactive compositions being ejected from the jet dispenser according to which of the plural activation devices is triggered.

96. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and a reservoir containing said bioactive composition and a fluid conduit to convey the bio active composition from the reservoir to the jet dispenser, wherein said fluid conduit comprises tubing.

97. An applicator for cutaneous delivery of a bioactive composition to a cutaneous target, comprising:

a jet dispenser comprising an orifice, and a container which holds and delivers the bioactive composition to said orifice for ejection therethrough;

a spacer positioned between the dispenser orifice and the target during ejection of the bioactive composition to the target; and a reservoir containing said bioactive composition and a fluid conduit to convey the bioactive composition from the reservoir to the jet dispenser, wherein said reservoir comprises a collapsible bladder.

* * * * *

UNITED STATES PATENT AND TRADEMARK OFFICE
CERTIFICATE OF CORRECTION

PATENT NO. : 6,723,077 B2
DATED : April 20, 2004
INVENTOR(S) : Pickup et al.

It is certified that error appears in the above-identified patent and that said Letters Patent is hereby corrected as shown below:

Column 19,
Line 53, delete "that";

Column 22,
Line 5, delete "therein" and insert in lieu thereof -- wherein --.

Signed and Sealed this

Tenth Day of August, 2004

JON W. DUDAS
*Acting Director of the United States Patent and Trademark Office*